(12) United States Patent
Arai et al.

(10) Patent No.: US 9,688,597 B2
(45) Date of Patent: Jun. 27, 2017

(54) METHOD FOR PRODUCING ALDEHYDE (71) Applicant: Kao Corporation, Tokyo (JP)

(72) Inventors: Tsubasa Arai, Wakayama (JP); Jun Kono, Wakayama (JP); Yoshiharu Ataka, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/035,586

(22) PCT Filed: Dec. 26, 2014

(86) PCT No.: PCT/JP2014/006498
§ 371 (c)(1),
(2) Date: May 10, 2016

(87) PCT Pub. No.: WO2015/098121
PCT Pub. Date: Jul. 2, 2015

(65) Prior Publication Data
US 2016/0289151 A1  Oct. 6, 2016

(30) Foreign Application Priority Data
Dec. 26, 2013 (JP) .................. 2013-268427

(51) Int. Cl.
| C07C 45/00 | (2006.01) |
| B01J 23/00 | (2006.01) |
| B01J 35/00 | (2006.01) |
| B01J 37/03 | (2006.01) |
| B01J 23/745 | (2006.01) |
| B01J 23/889 | (2006.01) |
| B01J 31/02 | (2006.01) |

(52) U.S. Cl.
CPC .......... *C07C 45/002* (2013.01); *B01J 23/745* (2013.01); *B01J 23/8892* (2013.01); *B01J 31/0275* (2013.01); *B01J 35/002* (2013.01); *B01J 37/035* (2013.01); *B01J 2231/763* (2013.01); *B01J 2523/00* (2013.01); *B01J 2531/005* (2013.01)

(58) Field of Classification Search
CPC ... C07C 45/002; B01J 23/745; B01J 23/8892; B01J 2231/763
USPC ......................................... 568/485
See application file for complete search history.

(56) References Cited

U.S. PATENT DOCUMENTS

| 2004/0242938 A1 | 12/2004 | Kanougi et al. |
| 2005/0272958 A1 | 12/2005 | Hasegawa et al. |
| 2010/0010268 A1 | 1/2010 | Shirasawa et al. |
| 2015/0284310 A1 | 10/2015 | Arai et al. |
| 2015/0344391 A1 | 12/2015 | Nishimura et al. |

FOREIGN PATENT DOCUMENTS

| CN | 1335201 A | 2/2002 |
| CN | 1415591 A | 5/2003 |
| CN | 1572368 A | 2/2005 |
| CN | 103285848 A | 9/2013 |
| GB | 739263 | 10/1955 |
| JP | 5-168928 A | 7/1993 |
| JP | 2005-342675 A | 12/2005 |
| JP | 2008-184452 A | 8/2008 |
| JP | 2010-99635 A | 5/2010 |
| JP | 2012-126676 A | 7/2012 |
| JP | 2014-9167 A | 1/2014 |
| JP | 2014-118394 A | 6/2014 |
| JP | 2014-139158 A | 7/2014 |

OTHER PUBLICATIONS

International Search Report and Written Opinion issued Mar. 25, 2015, in PCT/JP2014/006498 filed Dec. 26, 2014.

*Primary Examiner* — Sikarl Witherspoon
(74) *Attorney, Agent, or Firm* — Oblon, McClelland, Maier & Neustadt, L.L.P.

(57) ABSTRACT

Provided is a method for producing aldehydes that brings an excellent alcohol conversion and aldehyde selectivity while suppressing generation of aldol condensates, etc. The method for producing aldehydes includes a step of dehydrogenating primary alcohol in the presence of a catalyst composition. The catalyst composition is a first catalyst composition obtained by adding a potassium salt of a weak acid to a dehydrogenation catalyst containing copper as an active species.

20 Claims, 1 Drawing Sheet

METHOD FOR PRODUCING ALDEHYDE

CROSS REFERENCE TO RELATED APPLICATIONS

This application is a 371 of International Patent Application No. PCT/JP2014/006498, filed on Dec. 26, 2014, and claims priority to Japanese Patent Application No. 2013-268427, filed on Dec. 26, 2013.

FIELD OF THE INVENTION

The present invention relates to a method for producing aldehydes by dehydrogenating primary alcohol.

BACKGROUND OF THE INVENTION

Aldehydes are useful compounds as starting materials for chemical reaction and fragrance materials. Especially, aliphatic aldehydes having a specific molecular weight are useful as fragrance materials by themselves, and further used as starting materials for derivatives having different fragrance notes.

As methods for producing aldehydes, conventionally, dehydrogenation, oxidation reaction and the like that use alcohol as a starting material are known. Among these, since dehydrogenation is an endothermic reaction while oxidation reaction is an exothermic reaction, dehydrogenation is often adopted as the production method of aldehydes because thermal control of the reaction is easy. Accordingly, catalysts for dehydrogenation also have been studied.

For example, for the purpose of obtaining high-purity carbonyl compounds with a high yield by improving activity and selectivity, Patent Document 1 (JP 05(1993)-168928 A) discloses a dehydrogenation catalyst that includes, as a carrier, at least one kind selected from the group consisting of oxides and hydroxides of aluminum, silicon, titanium, zirconium, magnesium and iron, zeolite, and silica-alumina, wherein each metal has a specific atomic ratio.

For the purpose of producing aldehydes from alcohol with high selectivity, Patent Document 2 (JP 2010-99635 A) discloses a solid catalyst for synthesizing aldehydes through alcohol dehydrogenation. The catalyst includes copper as an active species, and a quantity of surface acid sites of the catalyst measured by a temperature-programmed desorption analysis of ammonia is 0.10 mmol/g or lower.

SUMMARY OF THE INVENTION

In the aldehyde production through alcohol dehydrogenation, both a conversion of alcohol as starting material and selectivity for aldehydes to be obtained need to be high. For improving the alcohol conversion, increasing the activity of a catalyst used in the reaction is considered effective, which however decreases the aldehyde selectivity. Further, when the activity of the catalyst used in the reaction is increased, an aldol condensation, which is a side reaction, occurs, resulting in generation of aldol condensates and the like, i.e., aldol condensates and saturated substances of the condensates. Incidentally, aldol condensates and the like cannot be chemically converted into alcohol, or reused.

An object of the present invention is to provide a method for producing aldehydes that brings an excellent alcohol conversion and aldehyde selectivity while suppressing generation of by-products such as aldol condensates.

DETAILED DESCRIPTION OF THE INVENTION

Figure 1:
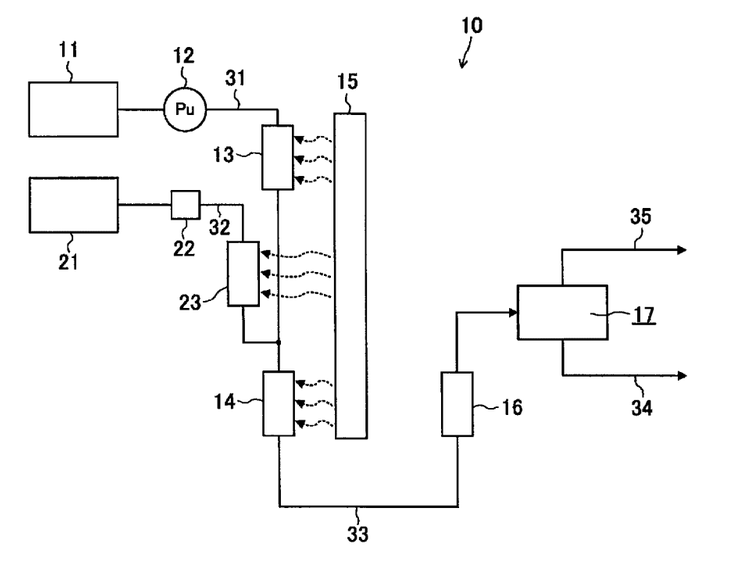
The FIGURE is a block diagram showing a reaction device used in Example 5.

The present inventors conducted studies based on the assumption that factors affecting the alcohol conversion, aldehyde selectivity and generation of aldol condensates and the like are conditions of the catalyst during dehydrogenation. As a result, the present inventors found that, in the aldehyde production in which a specific alcohol is dehydrogenated, by adding a potassium salt of a weak acid to a dehydrogenation catalyst containing copper as an active species, alcohol dehydrogenation can be performed with a high alcohol conversion and high aldehyde selectivity while suppressing generation of aldol condensates and the like.

Specifically, the present invention provides a method for producing an aldehyde, including a step of dehydrogenating primary alcohol in the presence of a catalyst composition. The catalyst composition is a first catalyst composition obtained by adding a potassium salt of a weak acid to a dehydrogenation catalyst containing copper as an active species.

Effect of the Invention

According to the present invention, it is possible to provide a method for producing aldehydes that brings an excellent alcohol conversion and aldehyde selectivity while suppressing generation of aldol condensates and the like.

The present invention relates to a method for producing an aldehyde that includes a step of dehydrogenating primary alcohol in the presence of a catalyst composition. The catalyst composition is a first catalyst composition obtained by adding a potassium salt of a weak acid to a dehydrogenation catalyst containing copper as an active species.

The following are possible explanations about why the method for producing an aldehyde according to the present invention allows production of aldehydes with an excellent alcohol conversion and aldehyde selectivity while suppressing generation of by-products such as aldol condensates.

In the present invention, aldehydes are obtained by dehydrogenating primary alcohol using a catalyst composition that is obtained by adding a potassium salt of a weak acid to a so-called copper-based dehydrogenation catalyst. Such a copper-based dehydrogenation catalyst includes acid sites, and excessive function of these acid sites proceeds a Tishchenko reaction of generated aldehydes, which results in disproportion of aldehydes with two molecules, generation of esters, and consequently reduction in aldehyde selectivity.

When a basic substance is added to the copper-based dehydrogenation catalyst for neutralizing the acid sites, the Tishchenko reaction is suppressed and the aldehyde selectivity is improved, whereas the catalyst activity in dehydrogenation decreases. Further, the added basic substance functions as a base catalyst and promotes an aldol condensation of generated aldehydes especially in dehydrogenation of primary alcohol, resulting in generation of aldol condensates and the like.

In the present invention, by adding a potassium salt of a weak acid having an adequate basicity and a relatively high electron donating property into the copper-based dehydrogenation catalyst, the salt can suppress the decrease in the catalyst activity and the function as a base catalyst while keeping the property of neutralizing acid sites. Further, since the electron donating ability thereof increases the electron density of the catalytic active sites, desorption of generated aldehydes from the catalyst is promoted, and hence the aldehyde selectivity is improved while suppressing progress of an aldol condensation without impairing a high alcohol conversion.

<Catalyst Composition>

In the present invention, the catalyst composition is a first catalyst composition obtained by adding a potassium salt of a weak acid to a dehydrogenation catalyst containing copper as an active species. The dehydrogenation catalyst is preferably composed of two components or three or more components containing copper and metallic elements other than copper. Preferable examples of the metallic elements other than copper include iron, zinc, chromium, cobalt, nickel, manganese, aluminum, silicon, and titanium. Among these, in terms of the aldehyde selectivity, environmental friendliness and safety, iron, chromium, manganese, aluminum and zinc are more preferred, iron, chromium, aluminum and manganese are further preferred, and iron is still further preferred. Examples of the dehydrogenation catalyst include CuFeAl, CuCrMn, and CuZnAl. Among these, CuFeAl and CuCrMn are preferred, and CuFeAl is more preferred.

It is preferable that the dehydrogenation catalyst is supported on a carrier. The carrier is preferably selected from the group consisting of oxides and hydroxides of aluminum, zinc, silicon, titanium and the like, zeolite, and silica-alumina. In terms of the aldehyde selectivity, the carrier is more preferably an oxide or a hydroxide of zinc or aluminum, and further preferably an oxide or a hydroxide of aluminum.

The dehydrogenation catalyst as a composition containing a carrier is preferably a catalyst containing copper-iron-aluminum (CuFeAl). The atomic ratio of the elements constituting the catalyst (copper/iron/aluminum) is preferably 1/0.4-2.5/0.5-5.0, and more preferably 1/0.5-1.0/1.5-3.5. Also, the dehydrogenation catalyst as a composition containing a carrier is preferably a catalyst containing copper-chromium-manganese (CuCrMn). The atomic ratio of the elements constituting the catalyst (copper/chromium/manganese) is preferably 1/0.5-2.0/0-0.5, and more preferably 1/0.7-1.3/0-0.3.

The dehydrogenation catalyst may be either calcinated or not calcinated. In the case of calcinating the dehydrogenation catalyst, the calcinating temperature is generally in a range of 100 degree C. or higher to 1200 degree C. or lower, and preferably in a range of 400 degree C. or higher to 900 degree C. or lower. The calcinating time is not limited particularly, and 10 hours or less is preferred from an economical viewpoint.

A quantity of surface acid sites of the dehydrogenation catalyst in the first catalyst composition measured by a temperature-programmed desorption analysis of ammonia is 0.10 mmol/g or more, preferably 0.11 mmol/g or more, and more preferably 0.12 mmol/g or more in terms of improving the alcohol conversion and aldehyde selectivity while suppressing generation of aldol condensates. From the same viewpoint, the quantity of surface acid sites of the dehydrogenation catalyst in the first catalyst composition measured by a temperature-programmed desorption analysis of ammonia is 0.20 mmol/g or less, preferably 0.16 mmol/g or less, more preferably 0.15 mmol/g or less, and further preferably 0.14 mmol/g or less. From the same viewpoint, the quantity of surface acid sites of the dehydrogenation catalyst in the first catalyst composition measured by a temperature-programmed desorption analysis of ammonia is in a range of 0.10 to 0.20 mmol/g, preferably in a range of 0.11 to 0.16 mmol/g, more preferably in a range of 0.12 to 0.15 mmol/g, and further preferably in a range of 0.12 to 0.14 mmol/g.

Also, a quantity of surface base sites of the dehydrogenation catalyst in the first catalyst composition measured by a temperature-programmed desorption analysis of carbon dioxide is preferably 0.65 mmol/g or more, and more preferably 0.70 mmol/g or more in terms of improving the alcohol conversion and aldehyde selectivity while suppressing generation of aldol condensates. From the same viewpoint, the quantity of surface base sites of the dehydrogenation catalyst in the first catalyst composition measured by a temperature-programmed desorption analysis of carbon dioxide is preferably 1.50 mmol/g or less, and more preferably 1.30 mmol/g or less. From the same viewpoint, the quantity of surface base sites of the dehydrogenation catalyst in the first catalyst composition measured by a temperature-programmed desorption analysis of carbon dioxide is preferably in a range of 0.65 to 1.50 mmol/g, and more preferably in a range of 0.70 to 1.30 mmol/g.

Further, a difference between the quantity of surface base sites and the quantity of surface acid sites of the dehydrogenation catalyst in the first catalyst composition is, e.g., in a range of 0.40 to 1.30 mmol/g, preferably in a range of 0.50 to 1.20 mmol/g, and more preferably in a range of 0.60 to 1.10 mmol/g in terms of improving the alcohol conversion and aldehyde selectivity while suppressing generation of aldol condensates.

In the production method of the present invention, in terms of improving the alcohol conversion and aldehyde selectivity, the potassium salt of the weak acid is preferably at least one selected from the group consisting of potassium carbonate, potassium acetate, and potassium hydrogencarbonate.

In the production method of the present invention, the addition amount of the potassium salt of the weak acid is preferably 0.1 mmol or more, more preferably 0.2 mmol or more, based on the total amount of 1 g of the metallic elements in the dehydrogenation catalyst, in terms of improving the alcohol conversion and aldehyde selectivity. From the same viewpoint, the addition amount of the potassium salt of the weak acid is preferably 1.0 mmol or less, more preferably 0.8 mmol or less, based on the total amount of 1 g of the metallic elements in the dehydrogenation catalyst. From the same viewpoint, the addition amount of the potassium salt of the weak acid is preferably 0.1 to 1.0 mmol, and more preferably 0.2 to 0.8 mmol based on the total amount of 1 g of the metallic elements in the dehydrogenation catalyst.

In the production method of the present invention, the catalyst composition is preferably a second catalyst composition obtained by calcinating the first catalyst composition. The calcinating temperature is generally in a range of 100 degree C. or higher to 1200 degree C. or lower, and preferably in a range of 400 degree C. or higher to 900 degree C. or lower.

The quantity of surface acid sites of the dehydrogenation catalyst in the second catalyst composition measured by the temperature-programmed desorption analysis of ammonia is preferably 0.10 mmol/g or more, more preferably 0.11 mmol/g or more, and further preferably 0.12 mmol/g or more in terms of improving the alcohol conversion and aldehyde selectivity while suppressing generation of aldol condensates. From the same viewpoint, the quantity of surface acid sites of the dehydrogenation catalyst in the second catalyst composition measured by the temperature-programmed desorption analysis of ammonia is preferably 0.20 mmol/g or less, more preferably 0.16 mmol/g or less, further preferably 0.15 mmol/g or less, and still further preferably 0.14 mmol/g or less. From the same viewpoint, the quantity of surface acid sites of the dehydrogenation catalyst in the second catalyst composition measured by the temperature-programmed desorption analysis of ammonia is preferably in a range of 0.10 to 0.20 mmol/g, more preferably in a range of 0.11 to 0.16 mmol/g, further preferably in a range of 0.12 to 0.15 mmol/g, and still further preferably in a range of 0.12 to 0.14 mmol/g.

Also, the quantity of surface base sites of the dehydrogenation catalyst in the second catalyst composition measured by the temperature-programmed desorption analysis of carbon dioxide is preferably 0.65 mmol/g or more, and more preferably 0.70 mmol/g or more in terms of improving the alcohol conversion and aldehyde selectivity while suppressing generation of aldol condensates. From the same viewpoint, the quantity of surface base sites of the dehydrogenation catalyst in the second catalyst composition measured by the temperature-programmed desorption analysis of carbon dioxide is preferably 1.50 mmol/g or less, and more preferably 1.30 mmol/g or less. From the same viewpoint, the quantity of surface base sites of the dehydrogenation catalyst in the second catalyst composition measured by the temperature-programmed desorption analysis of carbon dioxide is preferably in a range of 0.65 to 1.50 mmol/g, and more preferably in a range of 0.70 to 1.30 mmol/g.

Further, the difference between the quantity of surface base sites and the quantity of surface acid sites of the dehydrogenation catalyst in the second catalyst composition is, e.g., in a range of 0.40 to 1.30 mmol/g, preferably in a range of 0.50 to 1.20 mmol/g, and more preferably in a range of 0.60 to 1.10 mmol/g in terms of improving the alcohol conversion and aldehyde selectivity while suppressing generation of aldol condensates.

Also, the present invention provides a catalyst composition (first catalyst composition) for obtaining an aldehyde by dehydrogenating primary alcohol, the catalyst composition being obtained by adding a potassium salt of a weak acid to a dehydrogenation catalyst containing copper as an active species.

The first catalyst composition of the present invention is preferably obtained by mixing the dehydrogenation catalyst and the potassium salt of a weak acid. For example, the dehydrogenation catalyst and the potassium salt of the weak acid can be mixed by adding an aqueous solution of the potassium salt of the weak acid to the dehydrogenation catalyst, followed by stirring, and evaporating to dryness.

Alternatively, the present invention also provides a second catalyst composition obtained by mixing the dehydrogenation catalyst and the potassium salt of the weak acid, and thereafter calcinating the mixture. For example, the second catalyst composition is obtained by adding an aqueous solution of the potassium salt of the weak acid to the dehydrogenation catalyst, followed by stirring, evaporating to dryness, and thereafter calcinating, whereby the dehydrogenation catalyst and the potassium salt of the weak acid can be mixed and then calcinated. The calcinating temperature is generally in a range of 100 degree C. or higher to 1200 degree C. or lower, and preferably in a range of 400 degree C. or higher to 900 degree C. or lower. The calcinating time is not limited particularly, and 10 hours or less is preferred from an economical viewpoint.

The catalyst composition of the present invention (in the specification, the "catalyst composition" refers to both the first catalyst composition and the second catalyst composition) may be either in the form of powder or in the form of a film. The dehydrogenation catalyst may be a catalyst in which only a catalytic active substance is powdered, or may be supported on a carrier. The carrier is preferably selected from the group consisting of oxides and hydroxides of aluminum, zinc, silicon, titanium and the like, zeolite, and silica-alumina. In terms of the alcohol conversion, the carrier is more preferably an oxide or a hydroxide of zinc or aluminum, and further preferably an oxide of zinc or an oxide or a hydroxide of aluminum.

The catalyst composition in the form of a film is, e.g., a catalyst composition having a catalyst composition layer of 1 mm or less in thickness on a support. In this case, in terms of suppressing residence of alcohol in pores of the catalyst composition layer and obtaining high aldehyde selectivity, the thickness of the catalyst composition layer in the form of a film is preferably 400 micrometer or less, more preferably 100 micrometer or less, further preferably 50 micrometer or less, and still further preferably 30 micrometer or less. Further, in terms of securing the strength of the form of a film and obtaining durability in strength, the thickness of the catalyst composition layer in the form of a film is preferably 0.01 micrometer or more, and more preferably 1 micrometer or more.

As the structure of the film-type catalyst composition, any structure corresponding to the shape of a reactor can be selected. Examples of the film-type catalyst composition include a catalyst composition coating layer that is formed on a wall surface inside a tube, and a catalyst composition that is molded in a thin plate shape to partition the interior of a tube into a plurality of axial flow paths. Both of them can be used suitably for a tubular flow reactor. Also, the film-type catalyst composition may be a catalyst composition coating layer that is formed on a surface of an open fin-shaped flat plate mounted inside a vessel, or the like. Such a film-type catalyst composition can be used suitably for a vessel-type reactor. In terms of securing the surface of a catalyst body, on which a reaction starting material is supplied and a product is collected, as large as possible, and proceeding the reaction efficiently, the film-type catalyst composition is preferably provided on an aggregate of bundled tubes each having an inner diameter of several millimeters to several dozen millimeters, or on an inner wall surface of a honeycomb structural body having a cell density of several dozen cells to several hundred cells per square inch.

In order to form the film-type catalyst composition into the above structure, in terms of obtaining both a thin catalyst layer and a high mechanical strength, it is preferable to fix the catalyst composition on the surface of a support.

The support is preferably made of metal or other materials having stiffness, specific examples of which include a metallic foil, a carbon composite, clay and the like. Among these, a metallic foil is preferred. As the metallic foil, a copper foil, a stainless foil, an aluminum foil and the like are preferred, and a copper foil and a stainless foil are more preferred.

An example of the film-type catalyst composition is a catalyst obtained by coating a support with a mixture of a catalyst composition and a binder, and curing the binder to fix the catalyst composition on the support.

An example of the binder used herein is a macromolecular compound or an inorganic compound. Specific examples of the macromolecular compound include cellulosic resin such as carboxymethylcellulose and hydroxyethylcellulose, fluorine resin such as polytetrafluoroethylene and polyvinylidene fluoride, urethane resin, epoxy resin, polyester resin, phenol resin, melamine resin, silicon resin and the like. Specific examples of the inorganic compound include inorganic compound sols such as silica, alumina, and the like.

An exemplary method for obtaining the film-type catalyst composition is a method of forming a coating layer containing the catalyst composition on the surface of support such as a tubular, planar, or honeycomb support. As the coating method at this time, any conventionally known method can be used. Examples of the coating method include physical vapor deposition such as sputtering, chemical vapor deposition, and an impregnation method from a solution system as well as a method of applying a mixture of a catalyst composition and a binder using a bar coater, a blade, spraying, dipping, spinning, gravure, die-coating, or the like.

(Production of Dehydrogenation Catalyst)

The production method of the dehydrogenation catalyst in the present invention is not limited as long as the catalyst can promote dehydrogenation. The catalyst containing copper-iron-aluminum, which is a suitable mode of the catalyst, is preferably produced by a method in which the following first to third steps are performed in this order.

(First Step)

The first step is a step of suspending at least one kind selected from the group consisting of oxides and hydroxides of aluminum, silicon, titanium, zirconium, magnesium and iron, zeolite, and silica-alumina (hereinafter, referred to as a carrier) in an aqueous medium, and reacting a water-soluble copper salt and a water-soluble iron salt with an alkali substance in the suspension, thereby precipitating a copper compound and an iron compound on the surface of the carrier.

First, a water-soluble copper salt and a water-soluble iron salt are dissolved in water so that the atomic ratio of Cu/Fe is 1/0.4-2.5. In this aqueous solution, a carrier is suspended so that the atomic ratio of Cu/metallic atom of the carrier is 1/0.1-3.0. The suspension is heated to a temperature of 60 degree C. to 120 degree C., and an aqueous solution of an alkali substance in an amount corresponding to the total of equivalent numbers of copper and iron ions is added to the heated suspension, whereby a copper compound and an iron compound are precipitated on the surface of the catalyst carrier.

Examples of the water-soluble copper salt used in the present invention include cupric sulfate, cupric chloride, cupric nitrate and the like. A mixture of these also can be used. Examples of the water-soluble iron salt used in the present invention include ferrous sulfate, ferrous chloride, ferrous nitrate and the like. A mixture of these also can be used, but ferrous sulfate is suitable from an economical viewpoint.

An example of the alkali substance used in the present invention is a hydroxide or a carbonate of alkali metal or alkaline-earth metal. Although the method of adding the alkali substance to the suspension is not limited particularly, these alkali substances are generally added in the form of an aqueous solution considering operability. When a hydroxide of alkali metal or alkaline-earth metal is used as the alkali substance, it is desirable to drop it slowly so as not to impair filterability of the precipitated catalyst. In the present invention, it is suitable to use a carbonate of alkali metal. The concentration of these alkali substances can be selected arbitrarily. Considering productivity of the catalyst, a highly concentrated precipitant also can be used. For example, in the case of sodium carbonate, an aqueous solution containing sodium carbonate in a concentration of 20 to 23% by mass is appropriate.

As to the carrier used in the first step, i.e., at least one kind selected from the group consisting of oxides and hydroxides of aluminum, silicon, titanium, zirconium, magnesium and iron, zeolite, and silica-alumina, it may be used directly after being prepared in a reaction vessel, or it may be a carrier prepared separately in advance. It is preferable that these carriers have a relatively uniform particle diameter. An average particle diameter of the carrier is 0.1 micrometer to 500 micrometer, and preferably 0.4 micrometer to 50 micrometer. An exemplary method for preparing the carrier in the reaction vessel is a method of dissolving into water a ferric salt such as a sulfate, a nitrate, and a hydrochloride in an amount to be used as the carrier, and dropping therein a carbonate of alkali metal, e.g., a sodium carbonate aqueous solution, at a temperature of 60 degree C. or higher in an amount corresponding to an equivalent number of iron ions so as to neutralize the solution. In this method, by charging a copper salt and an iron salt into the slurry without purifying a generated precipitate, the first step can be performed continuously. If carriers having uniform properties are used, it is possible to produce a catalyst with further stable performance. Therefore, the use of carriers having uniform properties is further advantageous in industrial-scale production.

(Second Step)

The second step is a step of reacting water-soluble aluminum with an alkali substance in the suspension obtained in the first step, thereby precipitating an aluminum compound on the surface of solid particles present in the suspension obtained in the first step.

The second step is performed by: dropping, in the suspension obtained in the first step, (i) an aqueous solution of a water-soluble aluminum salt (where the Al amount in this case based on the water-soluble copper salt used in the first step, i.e. Cu/Al, is 1/0.1-5.0 and preferably 1/0.5-3.0 in the atomic ratio) and (ii) an alkali substance in an amount corresponding to an equivalent number of aluminum ions described in (i) above; and precipitating an aluminum compound while keeping the temperature of the suspension at 60 degree C. to 120 degree C.

Examples of the water-soluble aluminum salt described in (i) above include aluminum sulfate, aluminum chloride, aluminum nitrate, and various alums. Among these, aluminum sulfate is suitable. A mixture of these also can be used.

Examples of the alkali substance described in (ii) above include the alkali substances to be used in the first step. The method of adding the alkali substance is preferably addition in the form of an aqueous solution in terms of operability. The concentration of the alkali substance is not limited particularly, and an aqueous solution containing the alkali substance in a concentration of about 20% by mass is preferred from an economical viewpoint. In order to prevent a rapid change of pH of the suspension, the method of adding the alkali substance is preferably such that the aqueous solution described in (i) above and the alkali substance or the solution thereof described in (ii) above are added simultaneously to the suspension.

Exemplary embodiments of the second step are as follows: (a) precipitating only an aluminum compound; (b) precipitating an aluminum compound and a copper compound simultaneously; (c) precipitating an aluminum compound and a copper compound simultaneously in the first stage, and precipitating an aluminum compound in the second stage; d) repeating a combination of these steps several times. A suspension obtained in the above-described method is adjusted at a pH of 7.0 or higher, and aged for 0 to 8 hours.

(Third Step)

In the third step, the precipitate obtained in the second step is separated by an ordinary method and washed with water. The obtained slurry or powder is dried and calcinated as needed. The calcinating temperature is generally in a range of 100 degree C. or higher to 1200 degree C. or lower, and preferably in a range of 400 degree C. or higher to 900 degree C. or lower. The calcinating time is not limited particularly, and 10 hours or less is preferred from an economical viewpoint. The resultant after calcinating may be pulverized, but it can be used directly as a catalyst without pulverization.

<Step of Dehydrogenating Primary Alcohol in the Presence of the Catalyst Composition>

In the production method of the present invention, in terms of usability of generated aldehydes as fragrance materials, the primary alcohol is preferably an aliphatic alcohol with a carbon number of 4 to 15, and more preferably an aliphatic alcohol with a carbon number of 6 to 12.

The alcohol may be either a saturated aliphatic alcohol or an unsaturated aliphatic alcohol. In terms of usability of generated aldehydes as fragrance materials, a saturated aliphatic alcohol is preferred. Especially, a saturated aliphatic alcohol with a carbon number of 4 to 15 is preferred, and a saturated aliphatic alcohol with a carbon number of 6 to 12 is more preferred.

The alcohol has a straight chain, branched, or cyclic alkyl group or alkenyl group or alkynyl group. In terms of usability of generated aldehydes as fragrance materials, an alcohol having a straight chain or branched alkyl group is preferred, and an alcohol having a straight chain alkyl group is more preferred. Among these, an alcohol having a straight chain or branched alkyl group with a carbon number of 4 to 15 is preferred, and an alcohol having a straight chain alkyl group with a carbon number of 6 to 12 is more preferred.

Specific examples of the alcohol include butanol, hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propylheptyl alcohol, lauryl alcohol (dodecyl alcohol), myristyl alcohol, geraniol, cyclopentyl methanol, cyclopentenyl methanol, cyclohexyl methanol, cyclohexenyl methanol, and the like. Among these, in terms of usability of generated aldehydes as fragrances, hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propylheptyl alcohol, lauryl alcohol, myristyl alcohol and geraniol are preferred, and hexyl alcohol, octyl alcohol, nonyl alcohol, decyl alcohol, undecyl alcohol and lauryl alcohol are more preferred, and octyl alcohol, undecyl alcohol and lauryl alcohol are more preferred.

The step of dehydrogenating primary alcohol according to the production method of the present invention is performed at, e.g., 180 degree C. to 300 degree C. In terms of the alcohol conversion, the step of dehydrogenating primary alcohol is preferably performed at 200 degree C. or higher and 300 degree C. or lower. In other words, in terms of the alcohol conversion, the step is preferably performed at 200 degree C. or higher, and more preferably performed at 230 degree C. or higher. Further, from the same viewpoint, the step is preferably performed at 300 degree C. or lower, and more preferably performed at 270 degree C. or lower.

In terms of vaporizing products, the step of dehydrogenating primary alcohol according to the production method of the present invention is performed at an absolute pressure of, e.g., 13 to 102 kPa. When the carbon number of the alcohol as a starting material is 10 or less, the pressure of the dehydrogenation is preferably 80 to 102 kPa, and more preferably at 101 kPa, i.e., an atmospheric pressure. When the carbon number of the alcohol as a starting material is 11 or more, the pressure is preferably 13 to 60 kPa.

In the step of dehydrogenating primary alcohol according to the production method of the present invention, it is preferable to continuously extract aldehydes, i.e., reaction products, from a reaction vessel. By extracting aldehydes in this manner, it is possible to suppress aldehydes from contacting with a catalyst and proceeding to further reaction, so that deterioration of generated aldehydes can be avoided.

Also, in the production method of the present invention, the step of dehydrogenating primary alcohol in the presence of the catalyst composition so as to obtain aldehydes is not limited particularly as long as the primary alcohol can be brought into contact with the catalyst composition. The reaction may be either a liquid-phase reaction or a gas-phase reaction.

In the case that the step of dehydrogenating primary alcohol according to the production method of the present invention is the liquid-phase reaction, the solvent may be primary alcohol or other solvents inert to the reaction. Examples of the other solvents include hydrocarbons, ethers, amines and the like.

In the case that the step of dehydrogenating primary alcohol according to the production method of the present invention is the liquid-phase reaction, the ratio of the catalyst composition with respect to the primary alcohol may be, e.g., 1 to 100 parts by mass, and preferably 1 to 20 parts by mass based on 100 parts by mass of the primary alcohol.

The step of dehydrogenating primary alcohol according to the production method of the present invention may be performed by either a batch method or a continuous method.

Regarding the above-described embodiment, the present invention further discloses the following aldehyde production method.

<1> A method for producing an aldehyde, including a step of dehydrogenating primary alcohol in the presence of a catalyst composition, wherein the catalyst composition is a first catalyst composition obtained by adding a potassium salt of a weak acid to a dehydrogenation catalyst containing copper as an active species, and a quantity of surface acid sites of the dehydrogenation catalyst measured by a temperature-programmed desorption analysis of ammonia is in a range of 0.10 mmol/g or more to 0.20 mmol/g or less.

<2> The method for producing an aldehyde according to <1>, wherein the quantity of surface acid sites of the dehydrogenation catalyst in the first catalyst composition measured by the temperature-programmed desorption analysis of ammonia is preferably 0.11 mmol/g or more, and more preferably 0.12 mmol/g or more, preferably 0.16 mmol/g or less, more preferably 0.15 mmol/g or less, and further preferably 0.14 mmol/g or less, preferably in a range of 0.11 to 0.16 mmol/g, more preferably in a range of 0.12 to 0.15 mmol/g, and further preferably in a range of 0.12 to 0.14 mmol/g.

<3> The method for producing an aldehyde according to <1> or <2>, wherein a quantity of surface base sites of the dehydrogenation catalyst in the first catalyst composition measured by a temperature-programmed desorption analysis of carbon dioxide is preferably 0.65 mmol/g or more, and more preferably 0.70 mmol/g or more, preferably 1.50 mmol/g or less, and more preferably 1.30 mmol/g or less, preferably in a range of 0.65 to 1.50 mmol/g, and more preferably in a range of 0.70 to 1.30 mmol/g.

<4> The method for producing an aldehyde according to any one of <1> to <3>, wherein the dehydrogenation catalyst is supported on a carrier.

<5> The method for producing an aldehyde according to <4>, wherein the carrier is preferably selected from the group consisting of oxides and hydroxides of aluminum, zinc, silicon, titanium and the like, zeolite, and silica-alumina, more preferably an oxide or a hydroxide of zinc or aluminum, and further preferably an oxide or a hydroxide of aluminum.

<6> The method for producing an aldehyde according to any one of <1> to <5>, wherein the dehydrogenation catalyst is preferably composed of two components or three or more components containing copper and metallic elements other than copper, wherein the metallic elements other than copper are preferably iron, zinc, chromium, cobalt, nickel, manganese, aluminum, silicon and titanium, more preferably iron, chromium, manganese, aluminum and zinc, and further preferably iron, chromium, aluminum and manganese, and still further preferably iron.

<7> The method for producing an aldehyde according to any one of <1> to <6>, wherein the dehydrogenation catalyst is preferably CuFeAl, CuCrMn or CuZnAl, more preferably CuFeAl or CuCrMn, and further preferably CuFeAl.

<8> The method for producing an aldehyde according to any one of <1> to <6>, wherein the dehydrogenation catalyst as a composition containing a carrier is a catalyst containing copper-iron-aluminum (CuFeAl), and the atomic ratio of the elements constituting the catalyst (copper/iron/aluminum) is preferably 1/0.4-2.5/0.5-5.0, and more preferably 1/0.5-1.0/1.5-3.5.

<9> The method for producing an aldehyde according to any one of <1> to <6>, wherein the dehydrogenation catalyst as a composition containing a carrier is a catalyst containing copper-chromium-manganese (CuCrMn), and the atomic ratio of the elements constituting the catalyst (copper/chromium/manganese) is preferably 1/0.5-2.0/0-0.5, and more preferably 1/0.7-1.3/0-0.3.

<10> The method for producing an aldehyde according to any one of <1> to <9>, wherein the dehydrogenation catalyst is a calcinated dehydrogenation catalyst.

<11> The method for producing an aldehyde according to any one of <1> to <10>, wherein a difference between the quantity of surface base sites and surface acid sites of the dehydrogenation catalyst in the first catalyst composition is preferably in a range of 0.40 to 1.30 mmol/g, more preferably in a range of 0.50 to 1.20 mmol/g, and further preferably in a range of 0.60 to 1.10 mmol/g.

<12> The method for producing an aldehyde according to any one of <1> to <11>, wherein an addition amount of the potassium salt of the weak acid is preferably 0.1 mmol or more, more preferably 0.2 mmol or more, and preferably 1.0 mmol or less, more preferably 0.8 mmol or less, and preferably 0.1 to 1.0 mmol, and more preferably 0.2 to 0.8 mmol based on a total amount of 1 g of metallic elements in the dehydrogenation catalyst.

<13> The method for producing an aldehyde according to any one of <1> to <12>, wherein the catalyst composition is preferably a second catalyst composition obtained by calcinating the first catalyst composition.

<14> The method for producing an aldehyde according to any one of <1> to <13>, wherein the calcinating temperature is preferably in a range of 100 degree C. or higher to 1200 degree C. or lower, and more preferably in a range of 400 degree C. or higher to 900 degree C. or lower.

<15> The method for producing an aldehyde according to <13> or <14>, wherein a quantity of surface acid sites of the dehydrogenation catalyst in the second catalyst composition measured by a temperature-programmed desorption analysis of ammonia is preferably 0.10 mmol/g or more, more preferably 0.11 mmol/g or more, and further preferably 0.12 mmol/g or more, preferably 0.20 mmol/g or less, more preferably 0.16 mmol/g or less, further preferably 0.15 mmol/g or less, and still further preferably 0.14 mmol/g or less, preferably in a range of 0.10 to 0.20 mmol/g, more preferably in a range of 0.11 to 0.16 mmol/g, further preferably in a range of 0.12 to 0.15 mmol/g, and still further preferably in a range of 0.12 to 0.14 mmol/g.

<16> The method for producing an aldehyde according to any one of <13> to <15>, wherein a quantity of surface base sites of the dehydrogenation catalyst in the second catalyst composition measured by a temperature-programmed desorption analysis of carbon dioxide is preferably 0.65 mmol/g or more, and more preferably 0.70 mmol/g or more, preferably 1.50 mmol/g or less, and more preferably 1.30 mmol/g or less, preferably in a range of 0.65 to 1.50 mmol/g, and more preferably in a range of 0.70 to 1.30 mmol/g.

<17> The method for producing an aldehyde according to any one of <13> to <16>, wherein a difference between the quantity of surface base sites and the quantity of surface acid sites of the dehydrogenation catalyst in the second catalyst composition is preferably in a range of 0.40 to 1.30 mmol/g, more preferably in a range of 0.50 to 1.20 mmol/g, and further preferably in a range of 0.60 to 1.10 mmol/g.

<18> The method for producing an aldehyde according to any one of <1> to <17>, wherein the primary alcohol is preferably an aliphatic alcohol with a carbon number of 4 to 15, and more preferably an aliphatic alcohol with a carbon number of 6 to 12.

<19> The method for producing an aldehyde according to any one of <1> to <18>, wherein the primary alcohol is preferably a saturated aliphatic alcohol with a carbon number of 4 to 15, and more preferably a saturated aliphatic alcohol with a carbon number of 6 to 12.

<20> The method for producing an aldehyde according to any one of <1> to <19>, wherein the step of dehydrogenating primary alcohol is preferably performed at 180 degree C. to 300 degree C., more preferably performed at 200 degree C. or higher and 300 degree C. or lower, preferably performed at 200 degree C. or higher, and more preferably performed at 230 degree C. or higher, preferably performed at 300 degree C. or lower, and more preferably performed at 270 degree C. or lower.

<21> The method for producing an aldehyde according to any one of <1> to <20>, wherein the step of dehydrogenating primary alcohol is preferably performed at 13 to 102 kPa.

<22> The method for producing an aldehyde according to any one of <1> to <21>, wherein, when the carbon number of the alcohol as a starting material is 10 or less, the step of dehydrogenating primary alcohol is preferably performed at 80 to 102 kPa, and more preferably performed at 101 kPa, i.e., an atmospheric pressure.

<23> The method for producing an aldehyde according to any one of <1> to <21>, wherein, when the carbon number of the alcohol as a starting material is 11 or more, the step of dehydrogenating primary alcohol is preferably performed at 13 to 60 kPa.

<24> The method for producing an aldehyde according to any one of <1> to <23>, wherein, in the step of dehydrogenating primary alcohol, an aldehyde as a reaction product is continuously extracted from a reaction vessel.

<25> The method for producing an aldehyde according to any one of <1> to <24>, wherein the potassium salt of the weak acid is at least one selected from potassium carbonate, potassium acetate, and potassium hydrogencarbonate.

<26> The method for producing an aldehyde according to any one of <1> to <25>, wherein the step of dehydrogenating primary alcohol is a liquid-phase reaction or a gas-phase reaction.

<27> The method for producing an aldehyde according to <26>, wherein the step of dehydrogenating primary alcohol is a liquid-phase reaction, and the ratio of the catalyst composition with respect to the primary alcohol is preferably 1 to 100 parts by mass, and more preferably 1 to 20 parts by mass based on 100 parts by mass of the primary alcohol.

<28> A catalyst composition for obtaining an aldehyde by dehydrogenating primary alcohol, wherein the catalyst composition is obtained by adding a potassium salt of a weak acid to a dehydrogenation catalyst containing copper as an active species, and a quantity of surface acid sites of the dehydrogenation catalyst measured by the temperature-programmed desorption analysis of ammonia is in a range of 0.10 mmol/g or more to 0.20 mmol/g or less.

<29> The catalyst composition according to <28>, wherein the dehydrogenation catalyst is a calcinated dehydrogenation catalyst.

<30> The catalyst composition according to <29>, wherein the quantity of surface acid sites of the dehydrogenation catalyst measured by the temperature-programmed desorption analysis of ammonia is preferably 0.11 mmol/g or more, and more preferably 0.12 mmol/g or more, preferably 0.16 mmol/g or less, more preferably 0.15 mmol/g or less, and further preferably 0.14 mmol/g or less, preferably in a range of 0.11 to 0.16 mmol/g, more preferably in a range of 0.12 to 0.15 mmol/g, and further preferably in a range of 0.12 to 0.14 mmol/g.

<31> The catalyst composition according to any one of <28> to <30>, wherein the quantity of surface base sites of the dehydrogenation catalyst measured by a temperature-programmed desorption analysis of carbon dioxide is preferably 0.65 mmol/g or more, and more preferably 0.70 mmol/g or more, preferably 1.50 mmol/g or less, and more preferably 1.30 mmol/g or less, preferably in a range of 0.65 to 1.50 mmol/g, and more preferably in a range of 0.70 to 1.30 mmol/g.

<32> The catalyst composition according to any one of <28> to <31>, wherein the dehydrogenation catalyst is supported on a carrier.

<33> The catalyst composition according to <32>, wherein the carrier is preferably selected from the group consisting of oxides and hydroxides of aluminum, zinc, silicon, titanium and the like, zeolite, and silica-alumina, more preferably an oxide or a hydroxide of zinc or aluminum, and further preferably an oxide or a hydroxide of aluminum.

<34> The catalyst composition according to any one of <28> to <33>, wherein the dehydrogenation catalyst is preferably composed of two components or three or more components containing copper and metallic elements other than copper, wherein the metallic elements other than copper are preferably iron, zinc, chromium, cobalt, nickel, manganese, aluminum, silicon and titanium, more preferably iron, chromium, manganese, aluminum and zinc, and further preferably iron, chromium, aluminum and manganese, and still further preferably iron.

<35> The catalyst composition according to any one of <28> to <34>, wherein the dehydrogenation catalyst is preferably CuFeAl, CuCrMn or CuZnAl, more preferably CuFeAl or CuCrMn, and further preferably CuFeAl.

<36> The catalyst composition according to any one of <28> to <34>, wherein the dehydrogenation catalyst as a composition containing a carrier is a catalyst containing copper-iron-aluminum (CuFeAl), and the atomic ratio of the elements constituting the catalyst (copper/iron/aluminum) is preferably 1/0.4-2.5/0.5-5.0, and more preferably 1/0.5-1.0/1.5-3.5.

<37> The catalyst composition according to any one of <28> to <34>, wherein the dehydrogenation catalyst as a composition containing a carrier is a catalyst containing copper-chromium-manganese (CuCrMn), and the atomic ratio of the elements constituting the catalyst (copper/chromium/manganese) is preferably 1/0.5-2.0/0-0.5, and more preferably 1/0.7-1.3/0-0.3.

<38> The catalyst composition according to any one of <28> to <37>, wherein a difference between the quantity of surface base sites and surface acid sites of the dehydrogenation catalyst in the catalyst composition is preferably in a range of 0.40 to 1.30 mmol/g, more preferably in a range of 0.50 to 1.20 mmol/g, and further preferably in a range of 0.60 to 1.10 mmol/g.

<39> The catalyst composition according to any one of <28> to <38>, wherein the primary alcohol is preferably an aliphatic alcohol with a carbon number of 4 to 15, and more preferably an aliphatic alcohol with a carbon number of 6 to 12.

<40> The catalyst composition according to any one of <28> to <39>, wherein the primary alcohol is preferably a saturated aliphatic alcohol with a carbon number of 4 to 15, and more preferably a saturated aliphatic alcohol with a carbon number of 6 to 12.

<41> The catalyst composition according to any one of <28> to <40>, wherein the potassium salt of the weak acid is at least one selected from potassium carbonate, potassium acetate, and potassium hydrogencarbonate.

<42> A method for producing a catalyst composition for dehydrogenation for aldehyde production, including a step of mixing a potassium salt of a weak acid into a dehydrogenation catalyst containing copper as an active species, wherein a quantity of surface acid sites of the dehydrogenation catalyst measured by the temperature-programmed desorption analysis of ammonia is in a range of 0.10 mmol/g or more to 0.20 mmol/g or less.

<43> The method for producing a catalyst composition for dehydrogenation for aldehyde production according to <42>, wherein an addition amount of the potassium salt of the weak acid in the step of adding potassium salt of the weak acid to the dehydrogenation catalyst is preferably 0.1 mmol or more, more preferably 0.2 mmol or more, and preferably 1.0 mmol or less, more preferably 0.8 mmol or less, and preferably 0.1 to 1.0 mmol, and more preferably 0.2 to 0.8 mmol based on a total amount of 1 g of metallic elements in the dehydrogenation catalyst.

<44> The method for producing a catalyst composition for dehydrogenation for aldehyde production according to <42> or <43>, further including a step of calcinating a mixture of the dehydrogenation catalyst and the potassium salt of the weak acid.

EXAMPLES

In the following Examples and Comparative Examples, "%" refers to "% by mass" unless otherwise indicated.

<Alcohol Conversion and Aldehyde Selectivity>

The alcohol conversion and the aldehyde selectivity were calculated in accordance with the following formulae. For both of the properties, the larger value is better.

Alcohol conversion [%]=100−[GC area % of alcohol]

Aldehyde selectivity [%]=[GC area % of aldehyde]/(100−[GC area % of alcohol])×100

<Aldol Condensate Selectivity>

The aldol condensate selectivity was calculated in accordance with the following formula. For the aldol condensate selectivity, the smaller value is better.

Aldol condensate selectivity [%]=[GC area % of aldol condensate]/(100−[GC area % of alcohol])×100

Further, the following was used as a standard product for GC (gas chromatography): when using octyl alcohol as a starting material, aldol condensate was 2-hexyl-2-desenal (manufactured by TOKYO CHEMICAL INDUSTRY Co., Ltd.).

<Quantity of Surface Acid Sites Measured by Temperature-Programmed Desorption Analysis of Ammonia>

An ammonia adsorption TPD spectrum of the catalyst composition was measured using BELCAT-B manufactured by BEL Japan, Inc. The quantity of surface acid sites of the catalyst composition was calculated from an ammonia desorption peak area obtained at the catalyst temperature from 100 degree C. to 300 degree C.

<Quantity of Surface Base Sites Measured by Temperature-Programmed Desorption Analysis of Carbon Dioxide>

A carbon dioxide adsorption TPD spectrum of the catalyst composition was measured using BELCAT-B manufactured by BEL Japan, Inc. The quantity of surface base sites of the catalyst composition was calculated from a carbon dioxide desorption peak area obtained at the catalyst temperature from 100 degree C. to 300 degree C.

<Addition Amount of Potassium Salt of Weak Acid in Catalyst Composition>

An amount of potassium contained in the catalyst composition was measured by atomic absorption spectrometry. An amount of the potassium salt of the weak acid added to the dehydrogenation catalyst was calculated from the obtained amount of potassium. Then, an addition amount of the potassium salt of the weak acid based on the total amount of 1 g of metallic elements in the dehydrogenation catalyst was calculated.

<Catalyst Production>

Production Example 1

Production of Copper-Based Solid Catalyst

In a reactor with a reflux cooler, water (300 g), $CuSO_4.5H_2O$ (48 g), $FeSO_4.7H_2O$ (59 g) and aluminum hydroxide (trade name "HIGILITE (registered trademark) H-42M" manufactured by SHOWA DENKO K.K., 12.14 g) were charged, and heated to 95 degree C. while stirring. This state was retained for 1 hour while keeping the temperature of the mixture at 95 degree C. to 97 degree C. (Cu/Fe (atomic ratio)=1/0.75, Cu/Al of aluminum hydroxide (atomic ratio)=1/0.7). Next, while keeping the temperature, a solution (23% by mass) in which $Na_2CO_3$ (44.8 g, 1 equivalent based on the total of equivalent numbers of copper and iron ions) was dissolved in water (150 g) was dropped to the mixture in 80 minutes. A precipitate having a blue-green color, which could be recognized visually in the mixture, gradually discolored to brown, and finally discolored to black.

While keeping the temperature of the mixture at 95 degree C. to 97 degree C., a solution 1 (Cu/Fe (atomic ratio)=1/0.75, Cu/Al of aluminum hydroxide (atomic ratio)=1/0.7) in which $CuSO_4.5H_2O$ (4.8 g) and $Al_2(SO_4)_2.16H_2O$ (46.8 g) were dissolved in water (109.2 g) and a solution 2 (22% by mass, 1 equivalent based on the total of equivalent numbers of copper and iron ions) in which $Na_2CO_3$ (27.6 g) was dissolved in water (98.2 g) were dropped to the mixture simultaneously. The dropping of the solution 1 was completed in 60 minutes, and the dropping of the solution 2 was completed in 30 minutes. To this mixture, a solution in which $Al_2(SO_4)_2.16H_2O$ (23.4 g) was dissolved in water (53.5 g) was dropped in 30 minutes (Cu/Al of aluminum hydroxide (atomic ratio)=1/2.1). Further, to this mixture, 10% by mass of an NaOH aqueous solution was dropped so as to adjust the mixture at pH 10.5. Then the mixture was aged for 1 hour. After aging, the mixture was filtered under suction to obtain a precipitate. The obtained precipitate was washed three times with 450 mL of water, and the obtained solid was pulverized lightly. Thus, a copper-based solid catalyst (60.3 g) was obtained. The atomic ratio of the obtained copper-based solid catalyst was expressed by copper/iron/aluminum (atomic ratio)=1/0.7/2.8.

Production Example 2

Production of Another Copper-Based Solid Catalyst 30 g of the copper-based solid catalyst obtained in Production Example 1 was calcinated at 750 degree C. for 1 hour in air. Thus, a copper-based solid catalyst (26 g) of Production Example 2 was obtained. The atomic ratio of the obtained copper-based solid catalyst was expressed by copper/iron/aluminum (atomic ratio)=1/0.7/2.8.

Production Example 3

Production of Catalyst Composition Obtained by Adding Potassium Carbonate

The copper-based solid catalyst (50 g) obtained in Production Example 1 above was washed three times with 450 mL of water, and a solution in which potassium carbonate (1.25 g, potassium 18.1 mmol) was dissolved in water (50 g) was added therein. The mixture was stirred for 30 minutes, and evaporated to dryness. The obtained solid was pulverized lightly and calcinated at 750 degree C. for 1 hour in air. Thus, a catalyst composition (48 g) obtained by adding potassium carbonate was obtained. The addition amount of the potassium salt in the obtained catalyst composition was 0.36 mmol-potassium/g. Further, the quantity of surface acid sites of the obtained catalyst composition measured by the temperature-programmed desorption analysis of ammonia was 0.11 mmol/g, and the quantity of surface base sites of the obtained catalyst composition measured by the temperature-programmed desorption analysis of carbon dioxide was 0.71 mmol/g.

Production Example 4

Production of Another Catalyst Composition Obtained by Adding Potassium Carbonate To the copper-based solid catalyst (60 g) obtained in Production Example 2 above, a solution in which potassium carbonate (1.5 g, potassium 21.8 mmol) was dissolved in water (50 g) was added. The mixture was stirred for 30 minutes, and evaporated to dryness. The obtained solid was pulverized lightly. Thus, a catalyst composition (60.5 g) obtained by adding potassium carbonate was obtained. The addition amount of the potassium salt in the obtained catalyst composition was 0.36 mmol-potassium/g. Further, the quantity of surface acid sites of the obtained catalyst composition measured by the temperature-programmed desorption analysis of ammonia was 0.14 mmol/g, and the quantity of surface base sites of the obtained catalyst composition measured by the temperature-programmed desorption analysis of carbon dioxide was 0.86 mmol/g.

Production Example 5

Production of Another Catalyst Composition Obtained by Adding Potassium Carbonate (Step of Adding Alkali Metal Salt)
To the copper-based solid catalyst (60 g) obtained in Production Example 2 above, a solution in which potassium carbonate (3.0 g, potassium 43.5 mmol) was dissolved in water (50 g) was added. The mixture was stirred for 30 minutes, and evaporated to dryness. The obtained solid was pulverized lightly. Thus, a catalyst composition (61.0 g) obtained by adding potassium carbonate was obtained. The addition amount of the potassium salt in the obtained catalyst composition was 0.72 mmol-potassium/g. Further, the quantity of surface acid sites of the obtained catalyst composition measured by the temperature-programmed desorption analysis of ammonia was 0.12 mmol/g, and the quantity of surface base sites of the obtained catalyst composition measured by the temperature-programmed desorption analysis of carbon dioxide was 1.22 mmol/g.

Step of Producing Film-Type Catalyst Composition 75 parts by mass of the catalyst composition obtained by the step of adding alkali metal salt, 25 parts by mass of polytitanocarbosilane (trade name "Tyranno Coat (registered trademark) VN-100" manufactured by UBE INDUSTRIES, LTD.) as a binder, and 60 parts by mass of methyl ethyl ketone were mixed together in a ball mill to obtain a coating material. The coating material was coated on one surface of a copper foil (thickness: 40 micrometer, width: 15 cm×25 cm) (support) using a bar coater. The obtained coating material of catalyst composition on the copper foil was dried at 130 degree C. for 1 minute, and then heated at 250 degree C. in an air atmosphere for 90 minutes to cure the binder in the coating material. Similarly to the above, the coating material of catalyst composition was coated on the other surface of the copper foil, then dried and heated similarly to the above. As a result, a film-type catalyst composition in which catalyst composition layers each having a thickness of 20 micrometer were fixed on the both surfaces of the copper foil was obtained. The mass of the catalyst composition layer per unit area including the binder was 20.6 g/m$^2$, and the mass of the potassium carbonate-added copper-based solid catalyst of the catalyst composition layer per unit area was 16.1 g/m$^2$.

Production Example 6

Production of Catalyst Composition Obtained by Adding Sodium Carbonate

A catalyst composition of Production Example 6 obtained by adding sodium carbonate was obtained in the same manner as in Production Example 4 except that sodium carbonate was used instead of potassium carbonate. The addition amount of the sodium salt in the obtained catalyst composition was 0.36 mmol-sodium/g. Further, the quantity of surface acid sites of the obtained catalyst composition measured by the temperature-programmed desorption analysis of ammonia was 0.23 mmol/g, and the quantity of surface base sites of the obtained catalyst composition measured by the temperature-programmed desorption analysis of carbon dioxide was 0.90 mmol/g.

Production Example 7

Production of Catalyst Composition Obtained by Adding Potassium Hydroxide

A catalyst composition of Production Example 7 obtained by adding potassium hydroxide was obtained in the same manner as in Production Example 4 except that potassium hydroxide was used instead of potassium carbonate. The addition amount of the potassium salt in the obtained catalyst composition was 0.36 mmol-potassium/g. Further, the quantity of surface acid sites of the obtained catalyst composition measured by the temperature-programmed desorption analysis of ammonia was 0.09 mmol/g, and the quantity of surface base sites of the obtained catalyst composition measured by the temperature-programmed desorption analysis of carbon dioxide was 0.93 mmol/g.

Production Example 8

Production of Catalyst Composition Obtained by Adding Potassium Acetate

A catalyst composition of Production Example 8 obtained by adding potassium acetate was obtained in the same manner as in Production Example 4 except that potassium acetate was used instead of potassium carbonate. The addition amount of the potassium salt in the obtained catalyst composition was 0.36 mmol-potassium/g. Further, the quantity of surface acid sites of the obtained catalyst composition measured by the temperature-programmed desorption analysis of ammonia was 0.15 mmol/g, and the quantity of surface base sites of the obtained catalyst composition measured by the temperature-programmed desorption analysis of carbon dioxide was 0.90 mmol/g.

Production Example 9

Production of Another Catalyst Composition Obtained by Adding Potassium Carbonate)

A catalyst composition of Production Example 9 obtained by adding potassium carbonate was obtained in the same manner as in Production Example 3 except that a copper-chromium-manganese catalyst (trade name "N203" manufactured by JGC C&C, copper/chromium/manganese (atomic ratio)=1/1/0.1) was used instead of the copper-based solid catalyst obtained in Production Example 1 above. The addition amount of potassium in the obtained catalyst composition was 0.36 mmol-potassium/g. Further, the quantity of surface acid sites of the obtained catalyst composition measured by the temperature-programmed desorption analysis of ammonia was 0.02 mmol/g, and the quantity of surface base sites of the obtained catalyst composition measured by the temperature-programmed desorption analysis of carbon dioxide was 0.85 mmol/g.

<Aldehyde Production>

Example 1

Production of n-octyl Aldehyde by Liquid-Phase Reaction (Dehydrogenation Step)

To a separable flask (made of glass) having an internal volume of 500 ml, 15 g of the catalyst composition obtained by adding potassium carbonate in Production Example 3 was charged together with 200 g of octyl alcohol (trade name "KALCOL 0898" manufactured by Kao Corporation). While stirring the mixture, a nitrogen gas was blown into the flask at 101 kPa at a speed of 20 L/hour, and the temperature was raised to 195 degree C. A product generated in the separable flask was vaporized and discharged from a distillate outlet, and reached a cooler cooled at 20 degree C. The product passed through the cooler was separated in a fractionator and collected in a liquid product collector. The reaction was performed for 5 hours, and a reactant in the collector and a residue in the flask after the reaction were mixed. Thus, n-octyl aldehyde was obtained. Table 1 shows evaluation results of the obtained product.

Examples 2, 3 and Comparative Examples 1-3

Production of n-Octyl Aldehyde by Liquid-Phase Reaction

Aldehydes of Examples 2, 3 and Comparative Examples 1-3 were produced in the same manner as in Example 1 except that, instead of using the catalyst composition obtained by adding potassium carbonate in Production Example 3, the following catalyst compositions were used in the respective examples: the catalyst composition obtained by adding potassium carbonate in Production Example 4 (Example 2); the catalyst composition obtained by adding sodium carbonate in Production Example 6 (Comparative Example 1); the copper-based solid catalyst obtained in Production Example 2 (Comparative Example 2); the catalyst composition obtained by adding potassium hydroxide in Production Example 7 (Comparative Example 3); and the catalyst composition obtained by adding potassium acetate in Production Example 8 (Example 3). Table 1 shows evaluation results of the obtained products.

Comparative Example 4

Production of n-octyl Aldehyde by Liquid-Phase Reaction

An aldehyde of Comparative Example 4 was produced in the same manner as in Example 1 except that the another catalyst composition obtained by adding potassium carbonate in Production Example 9 was used instead of the catalyst composition obtained by adding potassium carbonate in Production Example 3. Table 1 shows evaluation results of the obtained product.

Example 4

Production of n-lauryl Aldehyde by Liquid-Phase Reaction

An aldehyde of Example 4 was produced in the same manner as in Example 1 except that the starting material was changed from octyl alcohol to lauryl alcohol (dodecyl alcohol) (trade name "KALCOL 2098" manufactured by Kao Corporation), and the reaction pressure was changed from 101 kPa to 13 kPa. Table 1 shows evaluation results of the obtained product.

Example 5

Production of n-octyl Aldehyde by Gas-Phase Continuous Reaction (Dehydrogenation Process)

The film-type catalyst composition obtained in Production Example 5 was bent into a corrugated plate shape. The bent film-type catalyst composition and a planar film-type catalyst composition were stacked alternately, and packed in a stainless reaction tube 14 (inner diameter: 28 mm, tube length: 150 mm, flow-type reactor) (packed amount of the catalyst composition: 2.9 g). A vaporization tube 13 (made of stainless, inner diameter: 2 mm, tube length: 1500 mm) and a gas preheating portion 23 were connected to an inlet of the reaction tube 14, and a cooling tube 16 and a fractionator 17 were connected to an outlet of the reaction tube 14 (see the FIGURE). The vaporization tube 13 and the gas preheating portion 23 were heated at 320 degree C. for 12 minutes using a heating portion 15. Octyl alcohol (trade name "KALCOL 0898" manufactured by Kao Corporation) was supplied from a starting material alcohol supply portion 11 to the reaction tube 14 via a starting material alcohol supply tube 31 at a speed of 20.8 g/hour and nitrogen was supplied from a gas supply portion 21 to the reaction tube 14 via a gas supply tube 32 at a speed of 31.8 L/hour. In this case, in the mixed gas of the vaporized octyl alcohol and nitrogen gas, the partial pressure of octyl alcohol was 10 kPa.

Thereafter, the internal temperature of the reaction tube 14 was raised to 250 degree C. by the heating portion 15. At this time, the reaction pressure was 101 kPa. A product generated inside the reaction tube 14 reached the cooler 16 cooled at 20 degree C. via a product collection tube 33. The product passed through the cooler 16 was separated in the fractionator 17, and extracted with time via a liquid product collection tube 34. Thus, n-octyl aldehyde was obtained. This reaction was performed continuously for 20 hours. Table 1 shows evaluation results of the obtained product.

TABLE 1

| | | | | Example 1 | Example 2 | Comparative Example 1 | Comparative Example 2 | Comparative Example 3 |
|---|---|---|---|---|---|---|---|---|
| Reaction conditions | | Primary alcohol | | Octyl alcohol | Octyl alcohol | Octyl alcohol | Octyl alcohol | Octyl alcohol |
| | Catalyst composition | Dehydrogenation catalyst containing copper | Form | Powder | Powder | Powder | Powder | Powder |
| | | | Metal | CuFeAl | CuFeAl | CuFeAl | CuFeAl | CuFeAl |
| | | | Binder | — | — | — | — | — |

TABLE 1-continued

|  |  |  | | | | | |
|---|---|---|---|---|---|---|---|
|  |  | Calcinating |  | Not calcinated | calcinated | calcinated | calcinated | calcinated |
|  |  | Production Example |  | 1 | 2 | 2 | 2 | 2 |
|  | Added salt |  |  | Potassium carbonate | Potassium carbonate | Sodium carbonate | None | Potassium hydroxide |
|  | Calcinating of composition |  |  | calcinated | Not calcinated | Not calcinated | Not calcinated | Not calcinated |
|  | Addition amount of metal salt | [mmol-metal/g] | 0.36 | 0.36 | 0.36 | — | 0.36 |
|  | Quantity of surface acid sites measured by temperature-programmed desorption analysis of ammonia | [mmol/g] | 0.11 | 0.14 | 0.23 | — | 0.09 |
|  | Quantity of surface base sites measured by temperature-programmed desorption analysis of carbon dioxide | [mmol/g] | 0.71 | 0.86 | 0.90 | — | 0.93 |
|  | Difference between the quantity of surface acid sites and the surface base sites | [mmol/g] | 0.60 | 0.72 | 0.67 | — | 0.84 |
|  | Production Example |  | 3 | 4 | 6 | — | 7 |
|  | Amount of catalyst composition | [g] | 15.0 | 15.0 | 15.0 | 15.0 | 15.0 |
|  | Reaction phase |  | Liquid phase | Liquid phase | Liquid phase | Liquid phase | Liquid phase |
|  | Partial pressure of alcohol | [kPa] | — | — | — | — | — |
|  | Alcohol supply speed | [g/h] | — | — | — | — | — |
| Results | Reaction temperature | [° C.] | 195 | 195 | 195 | 195 | 195 |
|  | Reaction pressure | [kPa] | 101 | 101 | 101 | 101 | 101 |
|  | Alcohol conversion | [%] | 59.2 | 59.0 | 56.1 | 50.1 | 54.2 |
|  | Aldehyde selectivity | [%] | 71.1 | 70.5 | 65.5 | 64.9 | 65.5 |
|  | Aldol condensate selectivity | [%] | 0.07 | 0.08 | 0.11 | 0.16 | 0.91 |

|  |  |  |  | Example 3 | Comparative Example 4 | Example 4 | Example 5 |
|---|---|---|---|---|---|---|---|
| Reaction conditions | Primary alcohol |  |  | Octyl alcohol | Octyl alcohol | Dodecyl alcohol | Octyl alcohol |
|  | Catalyst composition | Dehydrogenation catalyst containing copper | Form | Powder | Powder | Powder | Film |
|  |  |  | Metal | CuFeAl | CuCrMn | CuFeAl | CuFeAl |
|  |  |  | Binder | — | — | — | Tyranno Coat |
|  |  | Calcinating |  | calcinated | Not calcinated | Not calcinated | calcinated |
|  |  | Production Example |  | 2 | — | 1 | 2 |
|  | Added salt |  |  | Potassium acetate | Potassium carbonate | Potassium carbonate | Potassium carbonate |
|  | Calcinating of composition |  |  | Not calcinated | calcinated | calcinated | Not calcinated |
|  | Addition amount of metal salt | [mmol-metal/g] | 0.36 | 0.36 | 0.36 | 0.72 |
|  | Quantity of surface acid sites measured by temperature-programmed desorption analysis of ammonia | [mmol/g] | 0.15 | 0.02 | 0.11 | 0.12 |
|  | Quantity of surface base sites measured by temperature-programmed desorption analysis of carbon dioxide | [mmol/g] | 0.90 | 0.85 | 0.71 | 1.27 |
|  | Difference between the quantity of surface acid sites and the surface base sites | [mmol/g] | 0.75 | 0.83 | 0.60 | 1.10 |
|  | Production Example |  | 8 | 9 | 3 | 5 |
|  | Amount of catalyst composition | [g] | 15.0 | 15.0 | 15.0 | 3.0 |
|  | Reaction phase |  | Liquid phase | Liquid phase | Liquid phase | Gas phase |
|  | Partial pressure of alcohol | [kPa] | — | — | — | 10 |

TABLE 1-continued

| | | | | | | |
|---|---|---|---|---|---|---|
| Results | Alcohol supply speed | [g/h] | — | — | — | 20.8 |
| | Reaction temperature | [° C.] | 195 | 195 | 195 | 250 |
| | Reaction pressure | [kPa] | 101 | 101 | 13 | 101 |
| | Alcohol conversion | [%] | 58.7 | 53.8 | 58.6 | 73.0 |
| | Aldehyde selectivity | [%] | 70.1 | 70.4 | 70.8 | 96.5 |
| | Aldol condensate selectivity | [%] | 0.07 | 0.08 | 0.06 | 0.04 |

It was understood from Table 1 that, as compared with the aldehydes obtained by the production methods of Comparative Examples, all the aldehydes obtained by the production methods of Examples exhibited an excellent alcohol conversion and aldehyde selectivity while suppressing generation of aldol condensates and the like.

INDUSTRIAL APPLICABILITY

Since the production method of the present invention brings an excellent alcohol conversion and aldehyde selectivity while suppressing generation of aldol condensates and the like, it is possible to efficiently produce aldehydes, especially aliphatic aldehydes having a specific configuration and aldehydes with excellent smell. This production method can be used suitably as a production method of aldehydes useful as fragrance materials.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

REFERENCE SIGNS LIST

10 reaction device
11 starting material alcohol supply portion
12 starting material supply pump
13 vaporization tube
14 reaction tube
15 heating portion
16 cooling tube
17 fractionator
21 gas supply portion
22 gas flow rate regulator
23 gas preheating portion
31 starting material alcohol supply tube
32 gas supply tube
33 product collection tube
34 liquid product collection tube
35 exhaust gas discharge tube

The invention claimed is:

1. A method for producing an aldehyde, comprising dehydrogenating a primary alcohol in the presence of a catalyst composition,
wherein the catalyst composition is a first catalyst composition obtained by adding a potassium salt of a weak acid to a dehydrogenation catalyst comprising copper as an active species, and
a quantity of surface acid sites of the dehydrogenation catalyst measured by a temperature-programmed desorption analysis of ammonia is in a range of 0.11 mmol/g or more and 0.20 mmol/g or less.

2. The method for producing an aldehyde according to claim 1, wherein the quantity of surface acid sites of the dehydrogenation catalyst in the first catalyst composition measured by the temperature-programmed desorption analysis of ammonia is in a range of 0.11 mmol/g or more and 0.16 mmol/g or less.

3. The method for producing an aldehyde according to claim 1, wherein a quantity of surface base sites of the dehydrogenation catalyst in the first catalyst composition measured by a temperature-programmed desorption analysis of carbon dioxide is in a range of 0.65 mmol/g or more and 1.50 mmol/g or less.

4. The method for producing an aldehyde according to claim 3, wherein a difference between the quantity of surface base sites and surface acid sites of the dehydrogenation catalyst in the first catalyst composition is in a range of 0.40 to 1.30 mmol/g.

5. The method for producing an aldehyde according to claim 1, wherein the dehydrogenation catalyst is supported on a carrier.

6. The method for producing an aldehyde according to claim 5, wherein the carrier is an oxide or a hydroxide of zinc or aluminum.

7. The method for producing an aldehyde according to claim 1, wherein the dehydrogenation catalyst comprises at least two components that comprise a metallic element other than copper.

8. The method for producing an aldehyde according to claim 1, wherein the dehydrogenation catalyst is CuFeAl, CuCrMn or CuZnAl.

9. The method for producing an aldehyde according to claim 1, wherein the dehydrogenation catalyst comprises copper-iron-aluminum (CuFeAl), and the atomic ratio of the elements constituting the catalyst (copper/iron/aluminum) is 1/0.4-2.5/0.5-5.0.

10. The method for producing an aldehyde according to claim 1, wherein an addition amount of the potassium salt of the weak acid is in a range of 0.1 mmol or more and 1.0 mmol or less based on a total amount of 1 g of metallic elements in the dehydrogenation catalyst.

11. The method for producing an aldehyde according to claim 1, wherein the catalyst composition is a second catalyst composition obtained by calcinating the first catalyst composition.

12. The method for producing an aldehyde according to claim 1, wherein the primary alcohol is an aliphatic alcohol with a carbon number of 4 to 15.

13. The method for producing an aldehyde according to claim 1, wherein the primary alcohol is a saturated aliphatic alcohol with a carbon number of 4 to 15.

14. The method for producing an aldehyde according to claim 1, wherein said dehydrogenating of the primary alcohol is performed at a temperature of from 180 degree C. to 300 degree C.

15. The method for producing an aldehyde according to claim 1, wherein the potassium salt of the weak acid is at least one salt selected from the group consisting of potassium carbonate, potassium acetate, and potassium hydrogencarbonate.

16. A catalyst composition,
wherein the catalyst composition is obtained by adding a potassium salt of a weak acid to a dehydrogenation catalyst comprising copper as an active species, and
wherein a quantity of surface acid sites of the dehydrogenation catalyst measured by a temperature-programmed desorption analysis of ammonia is in a range of 0.11 mmol/g or more and 0.20 mmol/g or less.

17. The catalyst composition according to claim 16 wherein the quantity of surface acid sites of the dehydrogenation catalyst measured by the temperature-programmed desorption analysis of ammonia is in a range of 0.11 mmol/g or more and 0.16 mmol/g or less.

18. The catalyst composition according to claim 16, wherein the dehydrogenation catalyst comprises copper-iron-aluminum (CuFeAl), and the atomic ratio of the elements constituting the catalyst (copper/iron/aluminum) is 1/0.4-2.5/0.5-5.0.

19. A method for producing a catalyst composition, comprising mixing a potassium salt of a weak acid into a dehydrogenation catalyst comprising copper as an active species,
wherein a quantity of surface acid sites of the dehydrogenation catalyst measured by a temperature-programmed desorption analysis of ammonia is in a range of 0.11 mmol/g or more and 0.20 mmol/g or less.

20. The method for producing a catalyst composition according to claim 19, further comprising calcinating a mixture of the dehydrogenation catalyst and the potassium salt of the weak acid.

* * * * *